US011369393B2

(12) United States Patent
Tah et al.

(10) Patent No.: US 11,369,393 B2
(45) Date of Patent: Jun. 28, 2022

(54) ACTUATOR DEVICES AND SYSTEMS

(71) Applicant: Boston Scientific Scimed, Inc., Maple Grove, MN (US)

(72) Inventors: Richard Tah, Milford, MA (US); Brian MacLean, Cary, NC (US); Mark Hera, Holden, MA (US); Peter J. Pereira, Mendon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 586 days.

(21) Appl. No.: 15/916,491

(22) Filed: Mar. 9, 2018

(65) Prior Publication Data

US 2018/0256180 A1    Sep. 13, 2018

Related U.S. Application Data

(60) Provisional application No. 62/469,902, filed on Mar. 10, 2017.

(51) Int. Cl.
*A61B 1/00* (2006.01)
*A61B 1/018* (2006.01)
(Continued)

(52) U.S. Cl.
CPC .... *A61B 17/22031* (2013.01); *A61B 1/00133* (2013.01); *A61B 1/307* (2013.01);
(Continued)

(58) Field of Classification Search
CPC ............ A61B 17/22031; A61B 17/221; A61B 1/00133; A61B 1/307; A61B 1/00085;
(Continued)

(56) References Cited

U.S. PATENT DOCUMENTS 8,353,493 B2    1/2013 Golden et al.
2005/0182292 A1    8/2005 Suzuki
(Continued)

FOREIGN PATENT DOCUMENTS

CN    105578944 A    5/2016
CN    105662524 A    6/2016
(Continued)

OTHER PUBLICATIONS

International Search Report and Written Opinion for corresponding International Application No. PCT/US2018/021667, dated May 25, 2018 (14 pages).

(Continued)

*Primary Examiner* — Timothy J Neal
*Assistant Examiner* — William B Chou
(74) *Attorney, Agent, or Firm* — Bookoff McAndrews, PLLC

(57) ABSTRACT

Aspects of a device are described. One aspect is a device comprising: a housing having a first portion engageable with a scope, and a second portion engageable with a handle of a retrieval device; a platform that is movable relative to the housing, and engageable with a slider of the retrieval device; and a link assembly that is coupled the housing and the platform, and operable to move the platform and slider relative to the housing and handle. Aspects of related devices and systems also are described.

17 Claims, 3 Drawing Sheets

(51) Int. Cl.
  *A61B 17/22* (2006.01)
  *A61B 17/221* (2006.01)
  *A61B 1/307* (2006.01)
  *A61B 17/00* (2006.01)
  *A61B 17/29* (2006.01)

(52) U.S. Cl.
  CPC .......... *A61B 17/221* (2013.01); *A61B 1/0014* (2013.01); *A61B 1/00085* (2013.01); *A61B 1/018* (2013.01); *A61B 2017/0046* (2013.01); *A61B 2017/00367* (2013.01); *A61B 2017/00477* (2013.01); *A61B 2017/22034* (2013.01); *A61B 2017/2911* (2013.01); *A61B 2017/2919* (2013.01)

(58) Field of Classification Search
  CPC .................. A61B 1/0014; A61B 1/018; A61B 2017/00367; A61B 2017/0046; A61B 2017/00477; A61B 2017/22034; A61B 2017/2911; A61B 2017/2919
  See application file for complete search history.

(56) References Cited

U.S. PATENT DOCUMENTS

| | | | |
|---|---|---|---|
| 2005/0288551 A1 | 12/2005 | Callister et al. | |
| 2006/0116692 A1* | 6/2006 | Ward | A61B 17/2909 606/113 |
| 2007/0142846 A1* | 6/2007 | Catanese, III | A61B 17/0482 606/142 |
| 2008/0064925 A1* | 3/2008 | Gill | A61B 1/00167 600/109 |
| 2009/0018392 A1* | 1/2009 | Scholly | G02B 23/2476 600/109 |
| 2012/0253120 A1 | 10/2012 | Callister et al. | |
| 2013/0190561 A1* | 7/2013 | Oskin | A61B 1/00124 600/104 |
| 2014/0171735 A1 | 6/2014 | Galperin et al. | |
| 2014/0200403 A1* | 7/2014 | West | A61B 1/00133 600/104 |
| 2014/0257253 A1 | 9/2014 | Jemison | |
| 2014/0316202 A1* | 10/2014 | Carroux | A61B 1/0052 600/146 |
| 2014/0316203 A1* | 10/2014 | Carroux | A61B 1/00133 600/146 |
| 2015/0164307 A1 | 6/2015 | Galperin et al. | |
| 2016/0089008 A1 | 3/2016 | Simmons | |
| 2016/0166129 A1 | 6/2016 | Walish et al. | |
| 2017/0202570 A1* | 7/2017 | Shelton, IV | A61B 18/1447 |
| 2018/0168642 A1* | 6/2018 | Shelton, IV | A61B 90/03 |
| 2019/0083090 A1* | 3/2019 | Milo | A61B 17/0644 |
| 2019/0290314 A1* | 9/2019 | Gemer | A61B 17/24 |
| 2020/0405377 A1* | 12/2020 | Kappus | A61B 18/1445 |

FOREIGN PATENT DOCUMENTS

| | | |
|---|---|---|
| CN | 106214219 A | 12/2016 |
| JP | 2005328882 A | 12/2005 |

OTHER PUBLICATIONS

First Search issued in Chinese Application No. 2018800168441 dated Feb. 22, 2022 (1 page).

Office Action issued in Chinese Application No. 201880016844.1 dated Mar. 2, 2022 with English Translation (11 pages).

* cited by examiner

ACTUATOR DEVICES AND SYSTEMS

CROSS-REFERENCE TO RELATED APPLICATIONS

This patent application claims the benefit of priority under 35 U.S.C. § 119 to U.S. Provisional Patent Application No. 62/469,902, filed Mar. 10, 2017, which is herein incorporated by reference in its entirety.

TECHNICAL FIELD

Aspects of the present disclosure generally relate to medical devices and procedures. Particular aspects relate to actuator devices and systems.

BACKGROUND

During noninvasive procedures, a physician may use a scope and a retrieval device to engage objects in a body. For example, in ureteroscopic procedures, the physician may use a ureteroscope and a retrieval device to engage stones, stone fragments, and/or other foreign objects in a kidney, ureter, and/or bladder. One advantage of noninvasive procedures is that the body's normal openings and passages may be utilized. In ureteroscopic procedures, the physician may move the scope through the ureter toward a stone, advance an end effector (e.g., a basket) of the retrieval device toward the stone, and engage the stone with said end effector.

Many noninvasive procedures require at least two operators. For example, in ureteroscope procedures, the physician may control the scope while a physician's assistant controls the retrieval device. A third operator may be required to manipulate the end effector. Requiring multiple operators leads to communication gaps between operators, movement inefficiencies during the procedure, and delayed response times. These difficulties add time and expense. Aspects of this disclosure may remedy these difficulties, and/or address other aspects of the prior art.

SUMMARY

One aspect of the present disclosure is an actuator device. The actuator device may comprise: a housing having a first portion engageable with a scope, and a second portion engageable with a handle of a retrieval device; a platform that is movable relative to the housing, and engageable with a slider of the retrieval device; and a link assembly that is coupled the housing and the platform, and operable to move the platform and slider relative to the housing and handle.

According to this aspect, the first portion of the housing may be removably engageable with the scope. The second portion of the housing may be removably engageable with the handle. The first portion of the housing may be configured to achieve a snap-fit with the scope. For example, the first portion of the housing may comprise a pivot surface engageable with a corresponding pivot surface on the scope to achieve the snap-fit by pivoting the first portion relative to the scope. The second portion of the housing may be configured to achieve a snap-fit with the handle. For example, the second portion of the housing may comprise at least one retaining arm engageable with the handle to achieve the snap-fit. As a further example, the at least one retaining arm may comprise: a first pair of retaining arms at a proximal end of the housing; and a second pair of retaining arms at a distal end of the housing.

The housing may define a movement axis, and the platform may be movable relative to the housing in a direction parallel to the movement axis. The scope may define a scope axis that is substantially parallel with the movement axis. The housing may include an internal guiding ledge, and the platform may be slidable on the internal guiding ledge. The platform may be configured to achieve a snap-fit with the slider. For example, the platform may be configured to interlock with a surface feature of the slider to achieve the snap-fit. The link assembly may comprise a lever operable to move the platform between a first position and a second position. The link assembly may comprise a spring positioned to bias the platform into the first or second position. The link assembly also may be configured to incrementally move the platform between the first and second positions.

Another aspect of this disclosure is a medical device. The medical device may comprise: a housing with a first portion coupled to a scope, and a second portion coupled to a handle of a retrieval device; a platform that is movable relative to the housing, and engageable with a slider of the retrieval device; and a link assembly operable to move the platform and slider relative to the housing and handle.

In this aspect, the link assembly may comprise a lever operable to move the platform between a first position and a second position. The link assembly may comprise a spring positioned to bias the platform towards the first or second position. In some aspects, the retrieval device may further comprise a wire extending distally from the housing, and a sheath extending distally from the slider. In other aspects, the retrieval device may comprise an extension movable relative to the handle and the slider, a wire extending distally from the slider, and a sheath extending distally from the extension.

Yet another aspect of the present disclosure is a system comprising: a scope; a retrieval device including: a handle, and a slider movable relative to the handle; and an actuator device including: a housing having a first portion engageable with the scope, and a second portion engageable with the handle of the retrieval device; a platform that is movable relative to the housing, and engageable with the slider of the retrieval device; and a link assembly that is coupled the housing and the platform, and operable to move the platform and slider relative to the housing and handle.

In this aspect, the scope may comprise a sheath and a working channel extending therethrough. The retrieval device may comprise a wire extending distally from the housing or the slider. The wire may be insertable through the working lumen of the scope when the actuator device is engaged with the scope and the housing. The link assembly may be operable to move the platform and the slider between: a first position, wherein an end effector on the wire is collapsed; and a second position, wherein the end effector is expanded. For example, the end effector may be collapsed into the working lumen of the scope in the first position, and expanded out of the working lumen of the scope in the second position.

The scope may comprise an actuator configured to manipulate the sheath independent of the link assembly. In some aspects, the scope may comprise a sheath and a working channel extending therethrough; the retrieval device may comprise an extension movable relative to the handle and the slider, a wire extending distally from the slider, and a sheath extending distally from the extension; the wire and sheath may be insertable through the working lumen of the scope when the actuator device is engaged with the scope and the housing; the platform, slider, and extension may be movable together distally to move the wire and sheath distally relative to the working channel; and the extension may be movable proximally relative to the slider to move the sheath proximally relative to the wire.

It is understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure. Each drawing depicts one or more aspects of this disclosure, as follows.

DETAILED DESCRIPTION

Aspects of actuator devices and systems are now described. Some aspects are described with reference to noninvasive procedures, such as ureteroscopic procedures, wherein a ureteroscope and a retrieval device with an end effector are utilized to engage stones, stone fragments, and/or other foreign objects in a kidney, ureter, and/or bladder. References to a particular type of procedure, such as ureteroscopy; device, such as a retrieval device; end effector, such as a basket; organ, such as a kidney; and/or object, such as a stone or stone fragment, are provided for convenience and not intended to limit this disclosure. Accordingly, the concepts described herein may be utilized for any analogous device or system.

The directional terms "proximal" and "distal," and their respective initials "P" and "D," are utilized herein. Proximal refers to a position closer to the exterior of the body or a user, whereas distal refers to a position closer to the interior of the body or further away from the user. Appending the initials "P" or "D" to an element number signifies a proximal or distal location or direction. The term "elongated" may refer to any object that is substantially longer in relation to its width, such as an object having a length that is at least two times longer than its width along its longitudinal axis. Some elongated objects, for example, are axially extending in a proximal or distal direction along said axis. Unless claimed, these terms are provided for convenience and not intended to limit this disclosure to a particular location, direction, or orientation.

As used herein, terms such as "comprises," "comprising," or like variations, are intended to cover a non-exclusive inclusion, such that any aspect that comprises a list of elements does not include only those elements or steps, but may include other elements or steps not expressly listed or inherent thereto. Unless stated otherwise, the term "exemplary" is used in the sense of "example" rather than "ideal." Conversely, the terms "consists of" and "consisting of" are intended to cover an exclusive inclusion, such that an aspect that consists of a list of elements includes only those elements. As used herein, terms such as "about," "substantially," "approximately," or like variations, may indicate a range of values within +/−5% of a stated value.

Figure 1:
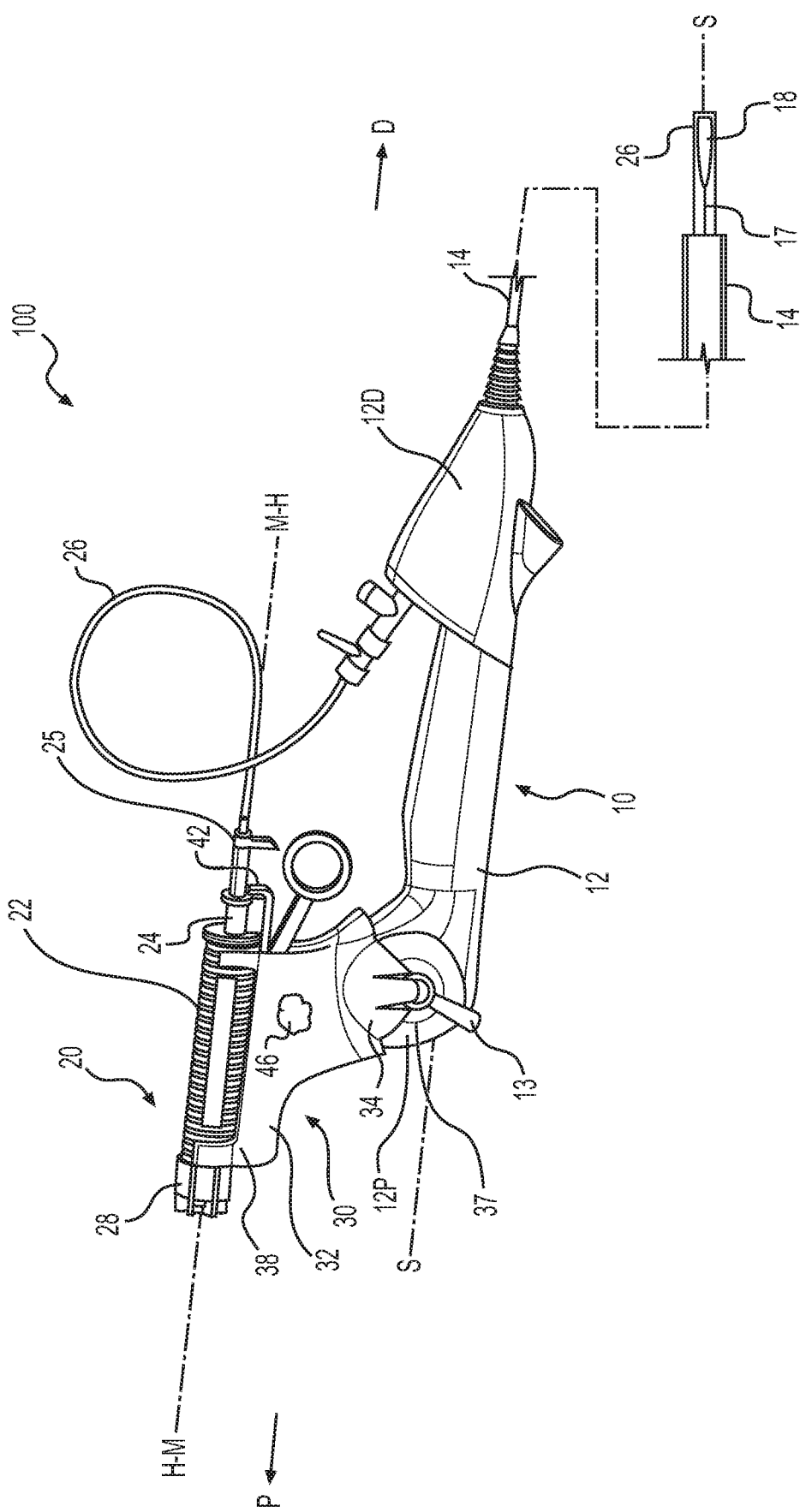
FIG. 1 depicts aspects of a system comprising examples of a scope, a retrieval device, and an actuator device.
Figure 2A:
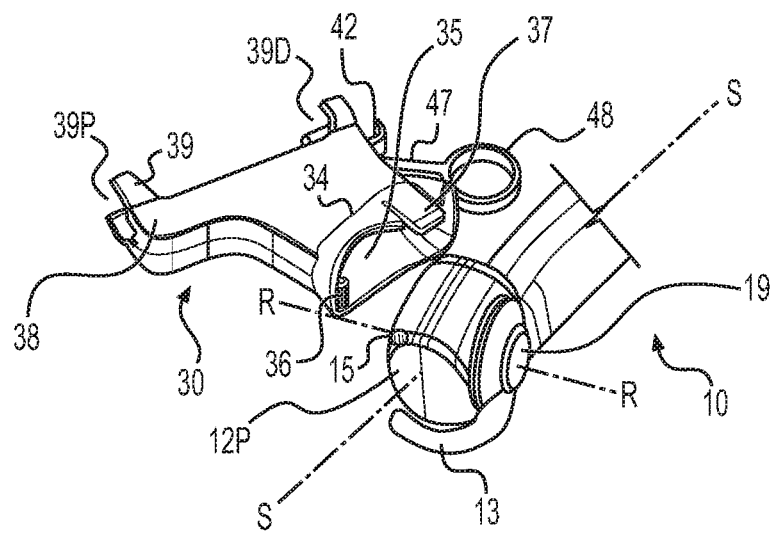
FIG. 2A depicts aspects of engaging the actuator device and the scope.
Figure 2B:
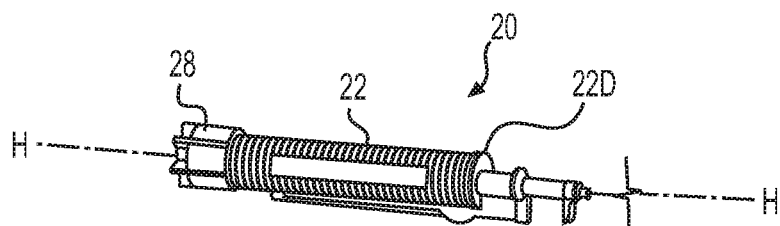
FIG. 2B depicts aspects of engaging the retrieval and actuator devices.
Figure 2B:
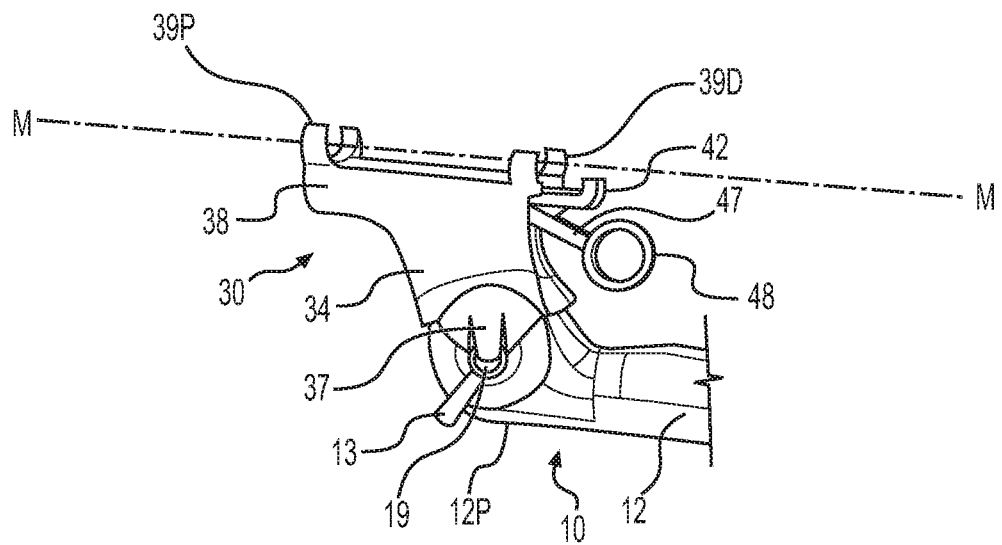
Figure 3:
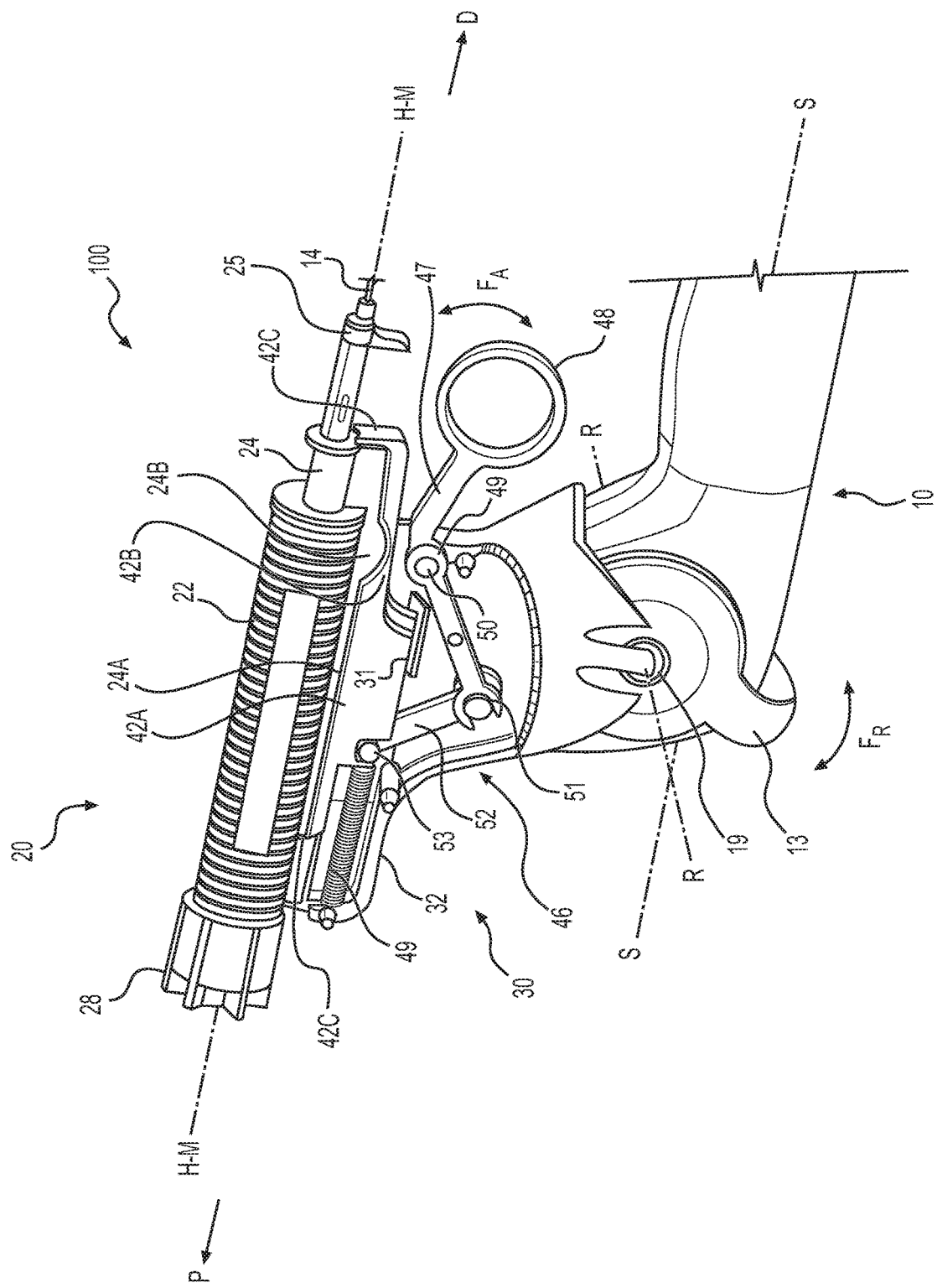
FIG. 3 depicts aspects of an exemplary link assembly of the actuator device, wherein a portion of housing of the actuator device has been removed.

Aspects of a system 100 are now described with reference to FIG. 1. As shown, system 100 may comprise: a scope 10, a retrieval device 20, and an actuator device 30. Aspects of engaging actuator device 30 with scope 10 and retrieval device 20 are depicted in FIGS. 2A and 2B; additional aspects of actuator device 30 are depicted in FIG. 3. Each element of system 100 is now described in turn.

Scope 10 may comprise any scope configured for use in non-invasive procedures, such as any ureteroscope sold by Boston Scientific® under the brand name Lithovue™. As shown in FIG. 1, scope 10 may comprise a scope body 12 extending along a scope axis S-S between a proximal end 12P and a distal end 12D. A scope sheath 14 may extend distally from distal end 12D. A working channel may extend through scope 10 and scope sheath 14, allowing a wire 17 (e.g., a wire, thread, rod, or similar elongated element) to be advanced through the scope 10 to a treatment site in a body, such as the interior of a kidney. In some aspects, scope 10 may comprise an actuator 13 configured to manipulate scope sheath 14. For example, as shown in FIG. 3, actuator 13 may be rotatable relative to handle 12 about a rotation axis R-R that is transverse with scope axis S-S. In this example, rotation of actuator 13 about rotation axis R-R may cause a distal end of scope sheath 14 to deflect away from scope axis S-S, allowing scope sheath 14 to be steered through the body.

Retrieval device 20 may comprise a handle or handle body 22, and a slider 24 movable relative to handle 22. Although not required, device 20 also may comprise a retrieval device sheath 26 extending distally around a portion of wire 17. Retrieval device sheath 26 may extend distally from a distal end of slider 24. For example, as shown in FIG. 1, device sheath 26 may extend distally from an extension 29 located on a distal end of slider 24. As also shown in FIG. 1, handle 22 may extend along a handle axis H-H, and slider 24 may move relative to handle 22 along handle axis H-H. In one aspect, wire 17 is coupled to handle 22, and retrieval device sheath 26 is coupled to slider 24, so that a distal end of wire 17 may be extended from sheath 26 by moving slider 24. For example, slider 24 may be movable from a first or distal position, wherein an end effector 18 on the distal end of wire 17 is collapsed into a distally extended sheath 26 (e.g., FIG. 1); to a second or proximal position, wherein end effector 18 is expanded from a proximally retracted sheath 26. End effector 18 may be a self-expandable basket made of a shape memory metal, similar to those sold by Boston Scientific® under the brand names Zero Tip® and Dakota®. Wire 17 may be coupled to handle 22 by an end cap 28.

Extension 29 may be moveable relative to slider 24. For example, the distal end of slider 24 may define a bore extending along handle axis H-H, and extension 29 may be movable (e.g., slidable) within the bore along axis H-H in a proximal-distal direction. In this example, wire 17 may be coupled to slider 24 (not to end cap 28), and retrieval device sheath 26 may be coupled to extension 29 (not to slider 24), allowing wire 17 and sheath 26 to be moved together distally by moving slider 24 distally with extension 29, and moved separately by moving extension 29 proximally relative to slider 24. For example, a distal end of sheath 14 may be located at a treatment site, allowing wire 17 and retrieval device sheath 26 to be manually fed distally through scope sheath 14 until a distal end of sheath 26 is adjacent the distal end of sheath 14. In this example, platform 42, slider 24, and extension 29 may be moved together distally until the distal end of device sheath 26 extends distally beyond the distal end of scope sheath 14, towards an object at the treatment site. Extension 29 may then be moved proximally relative to slider 24, collapsing retrieval device sheath 26 until end effector 18 is exposed and/or expanded to capture the object.

Actuator device 30 is configured to enable relative movements between scope 10 and slider 24. In some aspects, actuator device 30 may comprise: a housing 32 having a first portion 34 engageable with scope 10, and a second portion 38 engageable with handle 22; a platform 42 that is movable relative to housing 32, and engageable with slider 24; and an internal link assembly 46 that is coupled to housing 32 and platform 42, and operable to move platform 42 and slider 24 relative to housing 32 and handle 22. For example, as shown in FIG. 1, housing 32 may define a movement axis M-M, and platform 42 may be movable relative to housing 32 along axis M-M. Movement axis M-M may coincide with handle axis H-H when platform 42 is engaged with housing 22. In some aspects, as in FIG. 1, movement axis M-M housing 32 may be substantially parallel with scope axis S-S.

As shown in FIGS. 2A-B, actuator device 30 may be coupled to scope 10 and device 20 (e.g., fused together); or engageable with one or both of scope 10 and device 20 (e.g., snapped together). First portion 34 of housing 32 may be removably engageable with scope 12. For example, first portion 34 of housing 32 in FIG. 2A is configured to achieve the snap-fit with proximal end 12P of scope body 12. As shown, first portion 34 may comprise an interior cavity 35 sized to receive a portion of proximal end 12P. First portion 34 may comprise a pivot surface 36 engageable with a corresponding pivot surface 15 of scope 10 to achieve the snap-fit by pivoting actuator device 30 relative to said portion of proximal end 12P. For example, in FIG. 2A, pivot surface 36 is a protrusion, and corresponding pivot surface 15 is a curved indention on proximal end 12P that is engageable with surface 36 to properly position and allow for pivoting of actuator device 30 (e.g., about scope axis S-S) to achieve the snap-fit. The sidewalls of first portion 34 may be further configured (e.g., biased toward handle axis H-H) to grasp proximal end 12P.

Actuator 13 may be located on proximal end 12P of scope body 12, and first portion 34 of housing 32 may engage actuator 13 without limiting its operation. As shown in FIG. 2B, for example, first portion 34 may comprise a retaining arm 37 configured to grasp a portion of second actuator 13 without limiting its motion about rotation axis R-R. In this example, arm 37 may be configured to flex toward-and-away from movement axis M-M to rotatably engage a divot 19 formed on actuator 13, allowing actuator 13 to be rotated about axis R-R without interference from actuator device 30. Pivot surface 36 may be engageable with corresponding pivot surface 15 to rotate arm 37 into engagement with divot 19. Arm 37 may be biased toward divot 19.

The second portion 38 of housing 32 may be configured to achieve a snap-fit with handle 22 of retrieval device 20. For example, as shown in FIGS. 2A and 2B, second portion 38 may comprise at least one retaining arm 39 engageable with handle 22. At least one retaining arm 39 may comprise: a first or proximal pair of retaining arms 39P at the proximal end of housing 32; and a second or distal pair of retaining arms 39D at the distal end of housing 32. Any number of retaining arms 39 may be provided, at any position. Each retaining arm 39 may be configured to flex toward-and-away from movement axis M-M to achieve the snap-fit by grasping a portion of handle 22. For example, each pair of retaining arms 39P and 39D may be clamps configured to grasp an exterior surface of handle 22. In FIG. 2B, the interior surfaces of arms 39P and 39D may be configured (e.g., curved) to receive exterior surfaces of handle 22 (e.g., a cylindrical exterior surface). For example, the exterior surfaces of handle 22 in FIG. 2B comprise a plurality of parallel threads, and the interior surfaces of arms 39P and 39D may be configured to interlock with the plurality of threads.

Housing 22 may comprise an internal guiding ledge 31. In FIG. 3, for example, internal guiding ledge 31 comprises a plurality of internal surfaces of housing 22 that are configured to define a movement path for platform 42 along movement axis M-M. For example, a first or bottom surface of platform 42 may be moveable (e.g., slidable) on internal guiding ledge 31.

A second or top surface of platform 42 may be configured to receive a corresponding surface of slider 24, and/or achieve a snap-fit therewith. For example, as shown in FIG. 3, slider 24 may comprise: an elongated portion 24A, and a protrusion 24B extending outwardly from elongated portion 24A, allowing retrieval device 20 to be operated without actuator device 30 by grasping handle 22 in a hand, and operating slider 24 with a thumb of the hand. Accordingly, as shown in FIG. 3, the second surface of platform 42 may comprise: an elongated portion 42A configured to receive elongated portion 24A; a divot 42B configured to receive protrusion 24B; and/or a pair of endcaps 42C configured to receive the proximal and distal faces of slider 24. In this configuration, the snap-fit between slider 24 and platform 42 may be achieved by placing protrusion 24B in divot 42B, engaging a surface feature of elongated portion 24A with a corresponding feature of elongated portion 42A, and/or utilizing end caps 42C to apply a clamping force to the proximal and distal faces of slider 24.

As shown in FIG. 3, internal link assembly 46 may comprise a plurality of arms rotatably engaged with pivot points on housing 22 and/or platform 42. For example, link assembly 46 of FIG. 3 comprises a lever 47 operable to move platform 42 and slider 24 between the aforementioned first (or distal) and second (or proximal) positions along movement axis M-M. As shown, lever 47 may comprise a finger loop 48, a first pivot point 49 rotatably engaged with a pivot point 50 of housing 32, and a second pivot point 51 rotatably engaged with an arm 52 of link assembly 46. Arm 52 may, in turn, be rotatably engaged with a pivot point 53 of platform 42, such that application of actuation force $F_A$ to lever 47 in a first or distal-movement direction causes a corresponding distal movement of platform 42; and application of actuation force $F_A$ to lever 47 in a second or proximal-movement direction causes a corresponding proximal movement of platform 42.

Link assembly 46 may be configured to selectively control the position of platform 42 relative to housing 32. For example, in FIG. 3, link assembly 46 further comprises a spring 49 positioned to bias platform 42 in a proximal or distal direction. As shown in FIG. 3, a distal end of spring 49 may be rotatably engaged with pivot point 53 of platform 42, while a proximal end of spring 49 is engaged with housing 32. Internal guiding ledge 31, or an adjacent portion of housing 32, may comprise grooves or indentions configured to define additional and/or intermediate positions between said first and second positions. Link assembly 46 and/or lever 47 may further comprise additional springs or gears configured to provide additional controls, as well as a locking or ratcheting mechanism configured to fix a position of platform 42 relative to housing 32, and/or incrementally move platform 42 along movement axis M-M.

In some aspects, the first and second positions of platform 42 may correspond with the first and second positions of slider 24. For example, when platform 42 is engaged with slider 24, wire 17 is coupled to handle 22, and retrieval device sheath 26 is coupled to slider 24, then end effector 18 of wire 17 may be expanded from device sheath 26 by moving platform 42 proximally into the second position, wherein sheath 26 is retracted proximally; and collapsed into sheath 26 by moving platform 42 distally into the first position, wherein sheath 26 is extended distally (e.g., FIG. 1). If retrieval sheath 26 is omitted, then end effector 18 may be similarly expanded from scope sheath 14 by moving platform 42 proximally, or collapsed into sheath 14 by moving platform 42 distally.

According to this example, wire 17 and retrieval sheath 26 may be moved to a treatment site through scope sheath 14, and actuator 13 of scope 10 may be moved to steer at least a distal end of scope sheath 14 towards the treatment site. Because of actuator device 30, these movements may be performed by a single operator. For example, the single operator may grasp scope body 12 in a first hand (e.g., in a palm of the hand) so that lever 47 is operable by a first digit on the first hand (e.g., a trigger finger), and actuator 13 is operable by a second digit on the first hand (e.g., a thumb), leaving the second hand free.

In other aspects, where extension 29 is movable relative to handle 22 and slider 24, the aforementioned first and second positions of platform 42 may correspond with a position of scope sheath 14 relative to retrieval device sheath 26, and relative movements between handle 22 and extension 29 may correspond with a position of end effector 18 relative to device sheath 26. For example, platform 42 may be engaged with slider 24, wire 17 may be coupled to slider 24, and retrieval device sheath 26 may be coupled to extension 29. In this configuration, device sheath 26 may be moved to the treatment site through scope sheath 14, as before. In this example, however, platform 42, slider 24, and extension 29 may be moved together distally to advance retrieval device sheath 26 distally out of scope sheath 14; and extension 29 may be moved proximally relative to slider 24 to expand end effector 18 from device sheath 26. Actuator device 30 allows for single-handed operation in this configuration as well. For example, a single hand of the operator may be used to operate lever 47 and actuator 13, and then move extension 29 relative to slider 24.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. An actuator device comprising:
a housing having a first portion engageable with a scope and a second portion removably engageable with a handle of a retrieval device;
a platform that is movable relative to the housing and engageable with a slider of the retrieval device, wherein the platform extends distally from the second portion; and
a link assembly that is coupled to the housing and the platform, and operable to move the platform and slider relative to the housing and the handle, wherein the link assembly comprises a lever, the lever is between the scope and the retrieval device, and the lever is configured to be actuated in a first direction towards the scope and a second direction towards the retrieval device, wherein the first portion of the housing is configured to achieve a snap-fit with the scope.

2. The actuator device of claim 1, wherein the first portion of the housing is removably engageable with the scope.

3. The actuator device of claim 1, wherein the first portion of the housing comprises a pivot surface engageable with a corresponding pivot surface on the scope to achieve the snap-fit by pivoting the first portion relative to the scope.

4. The actuator device of claim 1, wherein the second portion of the housing is configured to achieve a snap-fit with the handle.

5. The actuator device of claim 4, wherein the second portion of the housing includes at least one retaining arm engageable with the handle to achieve the snap-fit.

6. The actuator device of claim 5, wherein the at least one retaining arm comprises:
a first pair of retaining arms at a proximal end of the housing; and
a second pair of retaining arms at a distal end of the housing.

7. The actuator device of claim 1, wherein the housing includes an internal ledge, and the platform is slidable on the internal ledge.

8. The actuator device of claim 1, wherein the platform includes a surface contoured to receive a corresponding surface of the slider.

9. The actuator device of claim 1, wherein the lever is operable to move the platform between a first position and a second position, and the link assembly further comprise a spring positioned to bias the platform into the first position.

10. A medical device comprising:
a housing with a first portion coupled to a scope, and a second portion removably coupled to a handle of a retrieval device;
a platform that is movable relative to the housing, and coupled to a slider of the retrieval device; and
a link assembly comprising a lever, wherein the link assembly is operable to move the platform and slider relative to the housing and the handle,
wherein the scope is configured to be grasped by a first hand of a user, the lever is between the scope and the retrieval device and the lever is configured to be actuated in a first direction towards the scope and a second direction towards the retrieval device, and the lever is operable by a finger of the first hand while the first hand is grasping the scope, wherein the second portion of the housing is configured to achieve a snap-fit with the handle of the retrieval device.

11. The medical device of claim 10, wherein the lever is operable to move the platform between a first position and a second position.

12. The medical device of claim 11, wherein the link assembly further comprises a spring positioned to bias the platform towards the first or second position.

13. The medical device of claim 11, wherein the retrieval device further comprises a wire extending distally from the housing, and a sheath extending distally from the slider.

14. The medical device of claim 11, wherein the retrieval device comprises an extension movable relative to the handle and the slider, a wire extending distally from the slider, and a sheath extending distally from the extension.

15. A system comprising:
a scope;

a retrieval device including:
   a handle, and
   a slider movable relative to the handle; and
an actuator device including:
   a housing having a first portion engageable with the scope, and a second portion removably engageable with the handle of the retrieval device;
   a platform that is movable relative to the housing, and engageable with the slider of the retrieval device; and
   a link assembly that is coupled the housing and the platform, wherein the link assembly comprises a lever and the link assembly is operable via the lever to move the platform and slider relative to the housing and handle,
wherein the lever is positioned between the scope and the retrieval device and the lever is configured to be actuated in a first direction towards the scope and a second direction towards the retrieval device,
wherein:
   the scope comprises a sheath and a working channel extending therethrough;
   the retrieval device comprises a wire extending distally from the housing or the slider; and
   the wire is insertable through the working lumen of the scope when the actuator device is engaged with the scope and the housing, and
   wherein the link assembly is operable to move the platform and the slider between:
      a first position, wherein an end effector on the wire is collapsed; and
      a second position, wherein the end effector is expanded.

16. The actuator device of claim 15, wherein the scope comprises an actuator configured to manipulate the sheath independent of the link assembly.

17. The actuator device of claim 15, wherein:
   the scope comprises a sheath and a working channel extending therethrough;
   the retrieval device comprises an extension movable relative to the handle and the slider, a wire extending distally from the slider, and a sheath extending distally from the extension;
   the wire and sheath are insertable through the working lumen of the scope when the actuator device is engaged with the scope and the housing;
   the platform, slider, and extension are movable together distally to move the wire and sheath distally relative to the working channel; and
   the extension is movable proximally relative to the slider to move the sheath proximally relative to the wire.

* * * * *